(12) United States Patent
Lattner et al.

(10) Patent No.: US 7,781,490 B2
(45) Date of Patent: Aug. 24, 2010

(54) PROCESS FOR THE PRODUCTION OF MIXED ALCOHOLS

(75) Inventors: James R. Lattner, LaPorte, TX (US); Michel Molinier, Houston, TX (US); Kun Wang, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 826 days.

(21) Appl. No.: 11/716,274

(22) Filed: Mar. 9, 2007

(65) Prior Publication Data

US 2007/0259972 A1     Nov. 8, 2007

Related U.S. Application Data

(60) Provisional application No. 60/798,383, filed on May 5, 2006.

(51) Int. Cl.
*C07C 27/00* (2006.01)

(52) U.S. Cl. .................. 518/700; 518/702; 518/703; 518/705; 518/713

(58) Field of Classification Search .................. 518/700, 518/702, 703, 705, 713
See application file for complete search history.

(56) References Cited

U.S. PATENT DOCUMENTS

| | | | |
|---|---|---|---|
| 4,122,110 | A | 10/1978 | Sugier et al. |
| 4,291,126 | A | 9/1981 | Sugier et al. |
| 4,592,806 | A | 6/1986 | Ilgner et al. |
| 6,444,712 | B1 | 9/2002 | Janda |
| 6,486,219 | B1 | 11/2002 | Janda et al. |

FOREIGN PATENT DOCUMENTS

| | | |
|---|---|---|
| WO | WO 02/26677 | 4/2002 |
| WO | WO 03/029174 | 10/2003 |

*Primary Examiner*—Jafar Parsa
(74) *Attorney, Agent, or Firm*—David M. Weisberg (57) ABSTRACT

The present invention relates to processes for forming mixed alcohols containing methanol and ethanol. The mixed alcohol can then be used as a feedstock for an oxygenate-to-olefin reaction system for conversion thereof to ethylene, propylene, and the like. In addition, the olefins produced by the oxygenate-to-olefin reaction can then be used as monomers for a polymerization of olefin-containing polymers and/or oligomers.

19 Claims, 1 Drawing Sheet

PROCESS FOR THE PRODUCTION OF MIXED ALCOHOLS

CROSS REFERENCE TO RELATED APPLICATION

This claims the benefit of and priority from U.S. Ser. No. 60/798,383, filed May 5, 2006. The above application is fully incorporated herein by reference.

FIELD OF THE INVENTION

The present invention relates to processes for forming mixed alcohols and processes for forming olefins from mixed alcohols, as well as processes for producing polyolefins therefrom. More particularly, the present invention relates to processes for forming a mixed alcohol feedstock containing at least methanol and varying amounts of ethanol

BACKGROUND OF THE INVENTION

Light olefins, defined herein as ethylene and propylene, are important commodity petrochemicals useful in a variety of processes for making plastics and other chemical compounds. Ethylene is used to make various polyethylene plastics, and in making other chemicals vinyl chloride, ethylene oxide, ethyl benzene, and alcohol. Propylene is used to make various polypropylene plastics, and in making other chemicals such as acrylonitrile and propylene oxide.

The petrochemical industry has known for some time that oxygenates, especially alcohols, are convertible into light olefins. The preferred conversion process is generally referred to as an oxygenates-to-olefin (OTO) reaction process. Specifically, in an OTO reaction process, an oxygenate contacts a molecular sieve catalyst composition under conditions effective to convert at least a portion of the oxygenates-to-light olefins. When methanol is the oxygenate, the process is generally referred to as a methanol-to-olefin (MTO) reaction process. Methanol is a particularly preferred oxygenate for the synthesis of ethylene and/or propylene.

Methanol is one of the major chemical raw materials, ranking third in volume behind ammonia and ethylene. Worldwide demand for methanol as a chemical raw material continues to rise especially in view of its increasingly important role (along with dimethyl ether) as a source of olefins such as ethylene and propylene and as an alternative energy source, for example, as a motor fuel additive or in the conversion of methanol to gasoline.

Methanol (as well as dimethyl ether) can be produced via the catalytic conversion of a gaseous feedstock comprising hydrogen, carbon monoxide, and carbon dioxide. Such a gaseous mixture is commonly referred to as synthesis gas or "syngas".

Methanol is typically produced from the catalytic reaction of syngas in a methanol synthesis reactor in the presence of a heterogeneous catalyst. For example, in one synthesis process, methanol is produced using a copper/zinc catalyst in a water-cooled tubular methanol reactor. In methanol production, syngas undergoes three reactions, only two of which are independent. These reactions are:

$$CO + 2H_2 \rightarrow CH_3OH \quad (A)$$

$$CO_2 + 3H_2 \rightarrow CH_3OH + H_2O \quad (B)$$

$$H_2O + CO \leftrightarrow H_2 + CO_2 \quad (C)$$

As can be seen from Reactions B and C, $CO_2$ can participate in methanol synthesis. Nevertheless, it is desirable to minimize the amount of $CO_2$ in the syngas for several reasons. In the first place, a low $CO_2$ content in the syngas results in a more reactive mixture for methanol synthesis provided the $CO_2$ content is at least about 2%. Furthermore, less $CO_2$ results in lower consumption of hydrogen and lower production of water. Lower water production is useful in applications where some relative small amounts of water can be present in the methanol product such as, for example, in connection with a methanol-to-olefins (MTO) process. Production of methanol with low water content thus eliminates the need to distill water from the syngas product methanol.

The syngas stoichiometry for methanol synthesis from syngas is generally described by the following relationship known as the "Stoichiometric Number" or $S_N$.

$$S_N = (H_2 - CO_2)/(CO + CO_2) \quad (D)$$

The value of $S_N$ theoretically required for methanol synthesis is 2.0. However, for commercial production of methanol from syngas, it is desirable that the value for $S_N$ range from about 1.95 to 2.15. Dimethyl ether (DME) may also be produced from syngas using chemistry similar to that used for methanol synthesis.

For example, U.S. Pat. Nos. 6,444,712 and 6,486,219 both describe methods for producing olefins from methanol, by way of using natural gas to make the methanol. The methods include converting the methane component of the natural gas to synthesis gas (syngas) using a steam reformer and a partial oxidation reformer. The syngas from each reformer is combined and sent to a methanol synthesis reactor. The combined syngas stream to the methanol synthesis reactor desirably has a syngas number of from about 1.4 to 2.6. The methanol product is then used as a feed in a methanol-to-olefin production process.

Autothermal reforming (ATR) involves the addition of air or oxygen with relatively smaller proportions of steam to a hydrocarbon feedstock. Reaction of hydrocarbon with oxygen proceeds according to the following general reaction schemes:

$$C_nH_m + (n/2)O_2 \leftrightarrow nCO + (m/2)H_2 \quad (E)$$

$$C_nH_m + (n + m/4)O_2 \leftrightarrow nCO_2 + (m/2)H_2O \quad (F)$$

When methane is the hydrocarbon undergoing oxidative reforming, these reactions become:

$$CH_4 + \tfrac{1}{2}O_2 \leftrightarrow CO + 2H_2 \quad (G)$$

$$CH_4 + 2O_2 \leftrightarrow CO_2 + 2H_2O \quad (H)$$

Autothermal reforming employs both steam reforming and oxidative reforming of the hydrocarbon feed. The exothermic oxidation of the feedstock hydrocarbons generates sufficient heat to drive the endothermic steam reforming reaction over the catalyst bed. The ATR procedure is thus run at relatively high temperatures and pressures with a relatively low steam to carbon ratio. The $CO_2$ content of the syngas from ATR processes, however, is fairly low, as is desirable for methanol synthesis.

Another known reforming process involves primarily partial oxidation of a hydrocarbon feed with an oxygen-containing gas. Catalytic partial oxidation reforming procedures are known; for purposes of this invention, partial oxidation reforming takes place in the absence of a catalyst. Due to the absence of a catalyst, partial oxidation (POX) reforming can operate at very high temperatures with little or no steam addition to the feedstock. Higher pressures than are used in ATR operations can be employed in POX reforming. However, the syngas composition resulting from POX reforming is generally deficient in hydrogen for methanol synthesis, resulting in $S_N$ and $H_2$:CO numbers below 2. On the other hand, the $CO_2$ content of the resulting syngas is generally very low which is below the optimum value for methanol synthesis.

Much of the methanol made today is made under high purity specifications. Grade A and grade AA methanol are commonly produced. U.S. Pat. No. 4,592,806 discloses a process for producing the grade AA methanol. The grade AA methanol has a maximum ethanol content of 10 ppm and is produced using a distillation column.

As the production of methanol continues to increase, and the new commercial uses of methanol also continue to increase, it would be advantageous to produce variable quality methanol streams, which have particular advantages for specific end uses, and which do not have to meet the stringent requirements of Grades AA and A methanol. It would also be beneficial to provide various processes for which the methanol streams would be of particular benefit.

Additionally, in many MTO reaction processes, the largest component of the oxygenate feedstock is methanol. However, relatively small amounts of oxygenates and/or higher alcohols, such as ethanol, can also be present in the feedstock. Some prior art MTO feedstocks have been treated to reduce the amounts of oxygenates and higher alcohols, while other prior art MTO feedstocks have been augmented to increase their relative content of higher alcohols and other oxygenates, for a variety of reasons. As a result, most prior art MTO processes utilize feedstocks that have undergone multiple processing and/or treatment steps to attain a higher proportion of higher alcohols, with respect to methanol.

In addition, when mixed alcohols are used as feedstocks in OTO reaction processes, water and carbon dioxide formation or retention can cause problems with olefin formation, e.g., reduced conversion efficiency. The prior art has recognized the benefit of reduction of water content and carbon dioxide content in OTO feedstock streams, but has taught complex combinations of process steps, creating increased cost and efficiency problems.

Thus, the need exists in the art for a process for producing a mixed alcohol MTO feedstock having a decreased carbon dioxide and/or water content and an increased proportion of ethanol to methanol with a minimum amount of processing.

SUMMARY OF THE INVENTION

One aspect of the invention relates to a process for producing a mixed alcohol product, said process comprising the steps of:
  a) contacting a feed stream comprising a syngas with a $CO_2$-lean mixed alcohol under process conditions sufficient to form a $CO_2$-lean syngas and a $CO_2$-rich mixed alcohol;
  b) contacting the $CO_2$-lean syngas with a mixed alcohol synthesis catalyst under conditions sufficient to form a liquid comprising a crude mixed alcohol composition and a gas comprising unreacted syngas; and
  c) removing $CO_2$ from the $CO_2$-rich mixed alcohol and the crude mixed alcohol composition, to form the mixed alcohol product, which comprises at least about 40 wt % methanol, at least about 3 wt % ethanol, and no more than about 1 mol % $CO_2$.

Advantageously, in one embodiment, a portion of the mixed alcohol product forms at least a portion of the $CO_2$-lean mixed alcohol.

In another embodiment, the $CO_2$-rich mixed alcohol and the crude mixed alcohol composition are combined before $CO_2$ removal.

In another embodiment, the feed stream further comprises at least a portion of the gas.

In another embodiment, the $CO_2$ removal from the $CO_2$-rich mixed alcohol and the crude mixed alcohol composition is accomplished by depressurization, distillation, or both.

In another embodiment, the process further comprises d) removing water from the feed stream before contacting with the $CO_2$-lean mixed alcohol for absorbing $CO_2$. In another embodiment, the water is removed by:
  (i) chilling the syngas to a temperature below about 0° C. and isolating condensed water therefrom;
  (ii) contacting the syngas with a $CO_2$-lean alcohol composition, or
  (iii) both (i) and (ii).

Additionally, in one embodiment, the syngas can be contacted with the $CO_2$-lean alcohol composition, and a portion of the mixed alcohol product can form at least a portion of the $CO_2$-lean alcohol composition. Additionally or alternately, in one embodiment, the condensed water can be isolated from the chilled syngas, and the condensed water, and optionally at least a portion of the $CO_2$-lean alcohol composition, can be recycled to the water removal step.

In another embodiment, the process further comprises:
  e) contacting natural gas, oxygen, and water under conditions sufficient to form the syngas; and
  f) recycling at least a portion of the $CO_2$, separated from the combined $CO_2$-rich mixed alcohol and crude mixed alcohol composition, for combining with the natural gas, oxygen, and water to form the syngas.

In another embodiment, the crude mixed alcohol composition and the $CO_2$-lean mixed alcohol each comprise at least about 40 wt % methanol and at least about 3 wt % ethanol. Additionally, in one embodiment, the crude mixed alcohol composition comprises one or more of the following:
  (i) at least about 50 wt % methanol;
  (ii) at least about 5 wt % ethanol;
  (iii) at least about 1 wt % of one or more $C_3$-$C_4$ monoalcohols;
  (iv) not more than about 3 wt % $CO_2$; and
  (v) from about 0.25 wt % to about 10 wt % water.

Additionally or alternately, in one embodiment, the mixed alcohol product, prior to any treatment step, if present, comprises one or more of the following:
  (i) at least about 50 wt % methanol;
  (ii) at least about 5 wt % ethanol;
  (iii) at least about 1 wt % of one or more $C_3$-$C_4$ monoalcohols;
  (iv) not more than about 0.8 wt % $CO_2$; and
  (v) from about 0.1 wt % to about 10 wt % water.

In another embodiment, the mixed alcohol synthesis catalyst comprises a copper-containing catalyst, preferably, a copper oxide.

In another embodiment, the contacting of the $CO_2$-lean syngas with the mixed alcohol synthesis catalyst occurs at a temperature from more than 250° C. to about 320° C. and at a pressure from about 30 barg (30.6 kg/cm² gauge) to about 150 barg (153 kg/cm² gauge).

In another embodiment, the contacting of the $CO_2$-lean syngas with the mixed alcohol synthesis catalyst occurs within a single reaction vessel.

An alternate process for producing a mixed alcohol product according to the invention comprises:

a) contacting a feed stream comprising a syngas with a $CO_2$-lean mixed alcohol under process conditions sufficient to form a $CO_2$-lean syngas and a $CO_2$-rich mixed alcohol;

b) contacting the $CO_2$-lean syngas with a mixed alcohol synthesis catalyst at a temperature from more than 250° C. to about 320° C. and at a pressure from about 30 barg (30.6 kg/cm$^2$ gauge) to about 150 barg (153 kg/cm$^2$ gauge) to form a liquid comprising a crude mixed alcohol composition and a gas comprising unreacted syngas; and c) removing $CO_2$ from the $CO_2$-rich mixed alcohol and the crude mixed alcohol composition, to form the mixed alcohol product, which comprises no more than about 1 mol % $CO_2$, wherein the $CO_2$-lean mixed alcohol and the mixed alcohol product each comprise at least about 40 wt % methanol and at least about 3 wt % ethanol.

An alternate process for producing a mixed alcohol product according to the invention comprises:

a) contacting a feed stream comprising a syngas with a $CO_2$-lean mixed alcohol under process conditions sufficient to form a $CO_2$-lean syngas and a $CO_2$-rich mixed alcohol;

b) contacting the $CO_2$-lean syngas with a mixed alcohol synthesis catalyst under conditions sufficient to form a liquid comprising a crude mixed alcohol composition and a gas comprising unreacted syngas; and c) removing $CO_2$ from the $CO_2$-rich mixed alcohol and the crude mixed alcohol composition, to form the mixed alcohol product, which comprises at least about 40 wt % methanol, at least about 3 wt % ethanol, and no more than about 1 mol % $CO_2$, wherein a portion of the mixed alcohol product forms at least a portion of the $CO_2$-lean mixed alcohol. Advantageously, the $CO_2$-lean syngas can be contacted with the mixed alcohol synthesis catalyst at a temperature from more than 250° C. to about 320° C. and at a pressure from about 30 barg (30.6 kg/cm$^2$ gauge) to about 150 barg (153 kg/cm$^2$ gauge).

Another aspect of the invention relates to a process for forming olefins from an oxygenate feed stream comprising mixed alcohols, which process comprises performing a mixed alcohol production process according to the invention, in order to form a mixed alcohol product that constitutes at least a portion of the oxygenate feed stream. In a preferred embodiment, the olefins formed from the mixed alcohol-containing oxygenate feed stream comprise both ethylene and propylene. Additionally or alternatively, in one embodiment, the mixed alcohol product is used in the oxygenate feed stream without any treatment to remove water from the mixed alcohol product.

Another aspect of the invention relates to a process for forming oligomers, homopolymers, copolymers, mixtures thereof, and/or blends thereof, by initiating and propagating a group of monomers comprising at least one olefin, which process comprises performing the an oxygenates-to-olefins process according to the invention, in order to form one or more olefins that constitute at least a portion of the at least one olefin in the group of monomers. Advantageously, the at least one olefin comprises ethylene, propylene, or both.

When process steps are enumerated by alphanumeric characters herein, it should be understood that their order in the recited process need not be set by the sequential nature of the list, i.e., sequential numbers/letters do not necessarily enumerate sequential steps.

Further, as described herein, it is contemplated that embodiments listed separately, even in different aspects of the invention described herein, may be combined together with one or more other embodiments, provided that the embodiments do not have features that are mutually exclusive.

DETAILED DESCRIPTION OF THE INVENTION

A. Introduction

One aspect of the present invention relates to a process for forming a mixed alcohol-containing feedstock product comprising both methanol and ethanol. The methanol and ethanol in the mixed alcohol product are both formed in a process for converting syngas to alcohols in the presence of a catalyst composition. The mixed alcohol product can be made from various carbon materials at a relatively large scale for commercial scale processing and upgrading. The alcohol-forming processes of this invention advantageously allow for transporting the manufactured and/or refined methanol/ethanol compositions to geographically distinct locations fairly remote from the site of manufacture for use as a feedstock to a variety of processes.

The processes by which the mixed alcohol product compositions or streams are made according to this invention result in an increased proportion of ethanol to methanol, in comparison to conventional methanol streams such as Grade AA and A methanol streams. The mixed alcohol product is particularly suitable for use as a feedstock for a variety of catalytic processes, particularly oxygenate-to-olefin (OTO) reaction processes, in which a mixed alcohol synthesis catalyst is used to convert the mixed alcohols to olefins, e.g., ethylene and/or propylene, preferably, including ethylene. The olefins can then be recovered and used for further processing, such as in the manufacture of polyolefins such as polyethylene and/or polypropylene, oligomers thereof, copolymers thereof, mixtures thereof, and/or blends thereof.

B. Methanol Synthesis Systems

1. Examples of Methanol Synthesis Processes

There are numerous technologies available for producing methanol including fermentation or the reaction of synthesis gas (syngas) derived from a hydrocarbon feed stream, which may include natural gas, petroleum liquids, carbonaceous materials including coal, recycled plastics, municipal waste, or any other organic material.

The hydrocarbon feed stream that is used in the conversion of hydrocarbon to syngas is optionally treated to remove impurities that can cause problems in further processing of the hydrocarbon feed stream. These impurities can poison many conventional propylene and ethylene forming catalysts. A majority of the impurities that may be present can be removed in any conventional manner. The hydrocarbon feed is preferably purified to remove sulfur compounds, nitrogen compounds, particulate matter, other condensables, and/or other potential catalyst poisons prior to being converted into syngas.

As mentioned above, the hydrocarbon feed stream may be supplied by any conventional means of syngas production, including, for example, autothermal reforming, partial oxidation, steam or $CO_2$ reforming, or a combination of these chemistries.

2. Syngas Production

Synthesis gas can be manufactured from a variety of carbon sources, although the main interest of the present invention is with natural gas feedstocks comprising methane. The reforming of hydrocarbons into syngas is an endothermic reaction, and heat must be supplied to make the reaction proceed. There are generally two methods of adding heat: (i) Indirect heating, generally by burning a fuel and transferring this heat across a metal membrane to the reaction zone, and (ii) In-situ heat generation by adding oxygen to the reformer feed, which results in exothermic oxidation reactions which supply heat for the endothermic. Steam is necessary in method (i), and is often called steam reforming. In method (ii), oxygen is always added, and will be referred to as "oxygen-blown" reforming. Various combinations of (i) and (ii) are possible, and will be referred to as "combined reforming".

Oxygen blown reforming may be operated with or without a catalyst. When no catalyst is used, the process will be referred to as Partial Oxidation, or POX The feedstock hydrocarbon and oxygen-containing gas are preheated and react in a burner. When catalyst is used, the oxygen-blown reforming may be further subdivided into two categories. If the feedstock hydrocarbon and oxygen-containing gas are pre-mixed, without reaction, before passing across a catalyst bed, the process will be referred to as Catalytic Partial Oxidation, or CPOX. When preheated feedstock and oxygen are combined in a burner, where exothermic reactions occur, before passing across a catalyst bed, the process will be referred to as Autothermal Reforming, or ATR.

Steam reformers operated with natural gas feedstock produce syngas that is rich in hydrogen, with stoichiometric numbers ($S_N$) approaching 3.0. Oxygen-blown reformers produce syngas that is less rich in hydrogen, and generally have $S_N$ values below the theoretical required value for methanol of 2.0. The present invention is directed at reforming processes that naturally produce sub-stoichiometric syngas, which includes any of the oxygen-blown reforming processes.

The amount of oxygen added to an oxygen-blown reformer depends upon the pressure, feed temperatures, feed compositions and diluent rates, and the desired level of conversion. The total molar flow rate of oxygen added to the reformer, divided by the flow rate of hydrocarbon-based carbon atoms fed to the reformer, will be referred to as the oxygen:carbon ratio.

Steam may be added to an oxygen-blown reformer, either as diluent to the hydrocarbon feedstock, diluent to the oxygen-containing gas, or may be directly injected into a specific portion of the reforming reactor to achieve localized cooling. The total molar flow rate of steam added to the oxygen-blown reformer in any manner, divided by the flow rate of hydrocarbon-based carbon atoms fed to the reformer, will be referred to as the steam:carbon ratio.

In the autothermal reforming of natural gas, steam is added to the feed as a means to reduce or eliminate soot formation, to cool select components of the burner within the ATR, and to reduce the methane content of the syngas at a given temperature. It is desirable to minimize the amount of steam added, so that less energy is required for generation of the steam, and so that the volume of gas passing through the reformer is minimized. ATR reactors generally require steam:carbon ratios of 1.2 to 2.0, although more recent technology allows operation in the 0.4 to 1.2 range. The oxygen:carbon ratio of an ATR ranges between 0.4 to 0.8, preferably, between 0.5 and 0.6.

In the partial oxidation of natural gas, the formation of soot is less of a concern because there is no catalyst bed to become fouled or plugged by the soot. Therefore, POX reformers can run with very little or no steam, with steam:carbon ratios between 0 and 0.2. The oxygen:carbon ratio of POX reformers ranges between 0.4 to 0.8, preferably, between 0.55 and 0.7.

The catalytic partial oxidation reforming process has not been commercialized to-date for methanol synthesis applications. A CPOX reforming process can theoretically operate with steam:carbon ratios below 0.2, or at any higher level of steam:carbon. A CPOX reformer will generally operate with an oxygen:carbon ratio between 0.4 and 0.8.

Any oxygen-blown reforming reactor will generally reach a product gas that approaches the most thermodynamically stable composition. One skilled in the art can calculate the adiabatic temperature and product syngas composition at thermodynamic equilibrium for any given feed composition, feed temperature, and pressure. The relative amounts of CO and $CO_2$ in the syngas is determined by the water gas shift (WGS) reaction equilibrium represented in Equation (C) above.

Increasing the level of steam added to the reformer will shift the reaction to the right, resulting in a greater proportion of $CO_2$ relative to CO. Higher reaction temperatures shift the equilibrium of the WGS to the left, resulting in reduced proportions of $CO_2$ relative to CO. It is easily shown that the stoichiometric number for methanol, $S_N$, is not affected by shifting between CO and $CO_2$ due to the WGS reaction. The $CO_2$ content of the syngas, however, is affected by the WGS reaction. Low levels of $CO_2$ in the syngas are favored by low steam:carbon and high temperatures in the reformer.

In the partial oxidation process, the catalyst comprises at least one transition element selected from the group consisting of Ni, Co, Pd, Ru, Rh, Ir, Pt, Os, and Fe. Preferably, the catalyst comprises at least one transition element selected from the group consisting of Pd, Pt, and Rh. In another embodiment, preferably, the catalyst, comprises at least one transition element selected form the group consisting of Ru, Rh, and Ir.

In one embodiment, the partial oxidation catalyst further comprises at least one metal selected from the group consisting of Ti, Zr, Hf, Y, Th, U, Zn, Cd, B, Al, Ti, Si, Sn, Pb, P, Sb, Bi, Mg, Ca, Sr, Ba, Ga, V, and Sc. Also, optionally, included in the partial oxidation catalyst is at least one rare earth element selected from the group consisting of La, Ce, Pr, Nd, Pm, Sm, Eu, Gd, Th, Dy, Ho, Er, Tm, Yb, and Lu.

In another embodiment, the catalyst employed in the process may comprise a wide range of catalytically active components, for example, Pd, Pt, Rh, Ir, Os, Ru, Ni, Cr, Co, Ce, La, and mixtures thereof. Materials not normally considered to be catalytically active may also be employed as catalysts, for example, refractory oxides such as cordierite, mullite, mullite aluminum titanate, zirconia spinels, and alumina.

In yet another embodiment, the catalyst is comprised of metals selected from those having atomic number 21 to 29, 40 to 47 and 72 to 79, the metals Sc, Ti, V, Cr, Mn, Fe, Co, Ni, Cu, Zr, Nb, Mo, Tc, Ru, Rh, Pd, Ag, Hf, Ta, W, Re, Os Ir, Pt, and Au. The preferred metals are those in Group 8 of the Periodic Table of the Elements, that is Fe, Os, Co, Re, Ir, Pd, Pt, Ni, and Ru.

In another embodiment, the partial oxidation catalyst comprises at least one transition or non-transition metal deposited on a monolith support. The monolith supports are preferably, impregnated with a noble metal such as Pt, Pd, or Rh, or other transition metals such as Ni, Co, Cr, and the like. Desirably, these monolith supports are prepared from solid refractory or ceramic materials such as alumina, zirconia, magnesia, ceria, silica, titania, mixtures thereof, and the like. Mixed refractory oxides, that is refractory oxides comprising at least two cations, may also be employed as carrier materials for the catalyst.

In one embodiment, the catalyst is retained in form of a fixed arrangement. The fixed arrangement generally comprises a fixed bed of catalyst particles. Alternatively, the fixed arrangement comprises the catalyst in the form of a monolith structure. The fixed arrangement may consist of a single monolith structure or, alternatively, may comprise a number of separate monolith structures combined to form the fixed arrangement. A preferred monolith structure comprises a ceramic foam. Suitable ceramic foams for use in the process are available commercially.

The partial oxidation process is operable over a wide range of pressures. For applications on a commercial scale, elevated pressures, that is pressures significantly above atmospheric pressure, are preferred. In one embodiment, the partial oxidation process is operated at pressures of greater than atmospheric up to about 150 barg (153 kg/cm$^2$ gauge). Preferably, the partial oxidation process is operated at a pressure in the range of from about 2 barg (2.04 kg/cm$^2$ gauge) to about 125 barg (127.5 kg/cm$^2$ gauge), more preferably, from about 5 barg (5.1 kg/cm$^2$ gauge) to about 100 barg (102 kg/cm$^2$ gauge).

The partial oxidation process is also operable over a wide range of temperatures. At the high operating pressures found at commercial scale, the exit temperature of the reaction zone should be high. In general, the higher the reaction pressure, the higher the required reactor exit temperature should be to achieve a desired conversion. In one embodiment, the exit temperature in excess of 600° C. Preferably, the exit temperature can be in the range of from about 600° C. to about 1,700° C., more preferably, from about 800° C. to about 1,600° C. The hydrocarbon and oxygen feeds are preferably, preheated separately prior to mixing.

3. Combination Syngas Processes

Combination reforming processes can also be incorporated into this invention. Examples of combination reforming processes include, but are not limited to, autothermal reforming and fixed-bed syngas generation. These processes involve a combination of gas phase partial oxidation and steam reforming chemistry.

The autothermal reforming process preferably, comprises two syngas generating processes, a primary oxidation process and a secondary steam reforming process. In one embodiment, a hydrocarbon feed stream is steam reformed in a tubular primary reformer by contacting the hydrocarbon and steam with a reforming catalyst to form a hydrogen and carbon monoxide containing primary reformed gas, the carbon monoxide content of which is further increased in the secondary reformer. In one embodiment, the secondary reformer includes a cylindrical refractory lined vessel with a gas mixer, preferably, in the form of a burner in the inlet portion of the vessel and a bed of nickel catalyst in the lower portion. In a more preferred embodiment, the exit gas from the primary reformer is mixed with air and residual hydrocarbons, and the mixed gas partially oxidized to carbon monoxides.

In an alternative embodiment of the invention, a fixed-bed syngas generation process is used to form syngas. In the fixed-bed syngas generation process, hydrocarbon feed and an oxygen-containing gas are introduced separately into a fluid catalyst bed. Preferably, the catalyst contains nickel and is supported, e.g., on alpha alumina.

The fixed-bed syngas generation process is typically carried out at elevated temperature and pressure conditions that favor the formation of hydrogen and carbon monoxide, when, e.g., methane is reacted with oxygen and steam. Preferably, the temperatures are in excess of about 1700° F. (927° C.), but not so high as to cause disintegration of the catalyst or the sticking of catalyst particles together. More preferably, the temperatures range from about 1750° F. (954° C.) to about 1950° F. (1066° C.), most preferably, from about 1800° F. (982° C.) to about 1850° F. (1010° C.).

Pressure in the fixed-bed syngas generation process may range from about atmospheric to about 40 atmospheres. In one embodiment, pressures from about 20 atmospheres to about 30 atmospheres are preferred, as that can facilitate compression of product gases for subsequent processes.

In one embodiment of the invention, the fluid-bed process is used with a nickel-based catalyst supported on alpha alumina. In another embodiment, silica is included in the support. The support, preferably, comprises at least 95 wt % alpha alumina, more preferably, at least about 98 wt % alpha alumina.

In one embodiment, a gaseous mixture of hydrocarbon feedstock and oxygen-containing gas are contacted with a reforming catalyst under adiabatic conditions. For the purposes of this invention, the term "adiabatic" refers to reaction conditions in which substantially all heat loss and radiation from the reaction zone is prevented, with the exception of heat leaving in the gaseous effluent stream of the reactor.

4. Converting Syngas to Mixed Alcohols

The syngas can advantageously be sent to a mixed alcohol synthesis process and converted to a crude mixed alcohol, e.g., comprising methanol and ethanol. In one embodiment, the syngas can be sent "as is" to the mixed alcohol synthesis process. In another embodiment, the hydrogen, carbon monoxide, and/or carbon dioxide content of the syngas can be adjusted for efficiency of conversion. Desirably, the syngas input to the methanol synthesis reactor has a molar ratio of hydrogen ($H_2$) to carbon oxides ($CO+CO_2$) in the range from about 0.5:1 to about 20:1, preferably, from about 2:1 to about 10:1. In another embodiment, the syngas has a molar ratio of hydrogen ($H_2$) to carbon monoxide (CO) of at least 2:1. Carbon dioxide is, optionally, present in an amount of not greater than 50 wt %.

Desirably, the stoichiometric molar ratio is sufficiently high so as to maintain the conversion of CO and $H_2$ to methanol, but not so high in $H_2$ as to reduce the volume productivity of methanol. Preferably, the synthesis gas fed to the methanol synthesis has a stoichiometric molar ratio [i.e., a molar ratio of $H_2:(2CO+3CO_2)$] from about 1.0:1 to about 2.7:1, more preferably, from about 1.1:1 to about 2.0:1, most preferably, from about 1.2:1 to about 1.8:1.

The $H_2$ content, relative to that of CO, in the syngas should typically be high enough to maintain an appropriately high reaction temperature and preferably, to minimize the amount of undesirable by-products such as paraffins. At the same time, the relative $CO_2$ to CO content should not be too high, so as to reduce methanol yield. In one embodiment, the syngas contains $CO_2$ and CO in a ratio from about 0.3:1 to about 1.2:1, preferably, from about 0.4:1 to about 1.0:1.

In a preferred embodiment, the mixed alcohol synthesis process includes: (a) contacting a feed stream comprising a syngas (e.g., formed according to one or more of the syngas formation processes described herein) with a $CO_2$-lean mixed alcohol under process conditions sufficient to form a $CO_2$-lean syngas and a $CO_2$-rich mixed alcohol; (b) contacting the $CO_2$-lean syngas with a mixed alcohol synthesis catalyst under conditions sufficient to form a liquid comprising a crude mixed alcohol composition and a gas comprising unreacted syngas; and (c) removing $CO_2$ from the $CO_2$-rich mixed alcohol and the crude mixed alcohol composition, to form the mixed alcohol product. Advantageously, the mixed alcohol product is preferably, $CO_2$-lean and comprises at least about 40 wt % methanol and at least about 3 wt % ethanol.

As used herein, the phrase "$CO_2$-lean" should be understood to mean having a $CO_2$ content of not more than about 1 mol % $CO_2$, and the phrase "$CO_2$-rich" should be understood to mean having a $CO_2$ content of not less than about 2 mol % $CO_2$, preferably, not less than about 3 mol %.

In addition, although at least some small amount of water can often be desirable in the mixed alcohol product according to the invention, increased amounts of water in the mixed alcohol product can directly and/or indirectly negatively impact use of the mixed alcohols in subsequent processes (e.g., OTO processes). As a result, in preferred embodiments, the water content of the mixed alcohol product can be less than about 20 wt %, preferably, less than about 15 wt %, more preferably, not more than about 10 wt %.

In one embodiment, the catalyst used in the mixed alcohol synthesis process includes an oxide of at least one element selected from the group consisting of copper, silver, zinc, boron, magnesium, aluminum, vanadium, chromium, manganese, gallium, palladium, osmium, and zirconium. In this embodiment, the catalyst is preferably, a copper-containing catalyst, more preferably, a copper oxide-containing catalyst.

In another embodiment, the catalyst used in the mixed alcohol synthesis process is a copper-containing catalyst, which includes an oxide of at least one element selected from the group consisting of silver, zinc, boron, magnesium, aluminum, vanadium, chromium, manganese, gallium, palladium, osmium, and zirconium. In this embodiment, the catalyst preferably, contains a copper oxide and an oxide of at least one element selected from the group consisting of zinc, magnesium, aluminum, chromium, and zirconium. In this embodiment, the catalyst more preferably, contains oxides of copper and zinc.

In yet another embodiment, the mixed alcohol synthesis catalyst comprises copper oxide, zinc oxide, and at least one other oxide. In this embodiment, the at least one other oxide is preferably, selected from the group consisting of a zirconium oxide, a chromium oxide, a vanadium oxide, a magnesium oxide, an aluminum oxide, a titanium oxide, a hafnium oxide, a molybdenum oxide, a tungsten oxide, and a manganese oxide.

In various embodiments, the mixed alcohol synthesis catalyst comprises from about 10 wt % to about 70 wt % of a copper oxide, based on total catalyst weight. In these embodiments, the mixed alcohol synthesis catalyst preferably, contains from about 15 wt % to about 68 wt % of a copper oxide, more preferably, from about 20 wt % to about 65 wt % of a copper oxide, based on total catalyst weight.

In one embodiment, the mixed alcohol synthesis catalyst comprises from about 3 wt % to about 30 wt % zinc oxide, based on total catalyst weight. In this embodiment, the mixed alcohol synthesis catalyst preferably, comprises from about 4 wt % to about 27 wt % of a zinc oxide, more preferably, from about 5 wt % to about 24 wt % of a zinc oxide, based on total catalyst weight.

In embodiments in which copper oxide and zinc oxide are both present in the mixed alcohol synthesis catalyst, the ratio of copper oxide to zinc oxide can vary over a wide range. In such embodiments, the mixed alcohol synthesis catalyst preferably exhibits a Cu:Zn atomic ratio from about 0.5:1 to about 20:1, more preferably, from about 0.7:1 to about 15:1, most preferably, from about 0.8:1 to about 5:1.

Methanol and mixed alcohol synthesis catalysts can be made according to conventional processes. Examples of such processes and catalysts can be found, e.g., in U.S. Pat. Nos. 6,114,279; 6,054,497; 5,767,039; 5,045,520; 5,254,520; 5,610,202; 4,666,945; 4,455,394; 4,565,803; and 5,385,949, with the descriptions of each being fully incorporated herein by reference.

In one embodiment, the syngas formed in the syngas conversion plant is cooled prior to sending to the mixed alcohol synthesis reactor, preferably, so as to condense at least a portion of the water vapor formed during the synthesis gas process.

The mixed alcohol synthesis process used to manufacture the mixed alcohol composition of this invention can include, but may not be limited to, batch processes, continuous processes, and the like. Continuous processes are preferred. Tubular bed processes and fluidized-bed processes are particularly preferred types of continuous processes.

In general, the methanol synthesis process takes place according to the reactions described in Equations A and B above. When the synthesis process involves simultaneous manufacture of mixed alcohols, the following reaction (along with the water-gas shift reaction; see Equation C above) typically applies:

$$n\text{CO} + 2n\text{H}_2 \rightarrow \text{C}_n\text{H}_{(2n+1)}\text{OH} + (n-1)\text{H}_2\text{O} \qquad (J)$$

In the case of methanol production, n=1, and thus Equation J reduces to Equation A, where no excess water is formed. However, for the production of higher alcohols, including ethanol (n=2), some excess water is formed [i.e., (n−1) moles] according to Equation J. The presence of excess water can have a detrimental effect on the reaction kinetics of the mixed alcohol synthesis process in Equation J, as its presence can limit the content of ethanol and $C_{3+}$ alcohols in the mixed alcohol product. Nevertheless, by making use of the water-gas shift reaction, excess water can advantageously consume carbon monoxide and be quickly converted to excess carbon dioxide and hydrogen gas, thus effectively removing excess water from the system and introducing excess carbon dioxide and hydrogen. Taking into consideration both Equations J and C, the disparity in hydrocarbon feedstock/reactant ($CO:H_2$) ratio can be adjusted for the water-gas shift reaction to maximize product, leaving only the effect of $CO_2$ on the reaction kinetics. Carbon dioxide, however, can be relatively easily separated from the mixed alcohol product, thus driving the reactions to completion and enabling a higher $C_{2+}$ alcohol (particularly ethanol) content.

The detrimental effects of excess water are expressed not only in the disruption of the reactant-product balance in Equation J, but also because water typically forms an azeotrope with $C_{2+}$ alcohols, in most cases requiring extensive distillation to recover those alcohols (see, e.g., Courty, P., et al., "Production of Methanol-Higher Alcohol Mixtures from Natural Gas Via Syngas Chemistry," Revue de Institut Francais du Petrole, 45(4), July-August 1990, pp. 561-78, relating to alcohol synthesis products with low water content used in hydrocarbon blends for motor gasoline). The processes of the present invention can advantageously avoid extensive distillation steps by utilizing the water-gas shift reaction and removing $CO_2$ during the processes, in order to drive the consumption of excess water.

The mixed alcohol synthesis process can desirably be effective over a wide range of temperatures. In one embodiment, the syngas is contacted with the mixed alcohol synthesis catalyst at a temperature from about 150° C. to about 450° C., preferably, from about 175° C. to about 350° C., more preferably, from about 200° C. to about 320° C. In another embodiment, the contacting of the syngas with the mixed alcohol synthesis catalyst occurs at a temperature from more than 250° C. to about 320° C., for example, from about 260° C. to about 310° C.

The process can also desirably be operable over a wide range of pressures. In one embodiment, the syngas is contacted with the mixed alcohol synthesis catalyst at a pressure from about 15 atm to about 125 atm, preferably, from about 20 atm to about 100 atm, more preferably, from about 25 atm to about 75 atm. In another embodiment, the contacting of the syngas with the mixed alcohol synthesis catalyst occurs at a pressure from about 30 barg (30.6 kg/cm$^2$ gauge) to about 150 barg (153 kg/cm$^2$ gauge), for example, from about 35 barg (35.7 kg/cm$^2$ gauge) to about 130 barg (132.6 kg/cm$^2$ gauge).

Gas hourly space velocities can vary depending upon the type of continuous process that is used. In one embodiment, gas hourly space velocity of flow of gas through the catalyst bed can be from about 50 hr$^{-1}$ to about 50,000 hr$^{-1}$. In this embodiment, gas hourly space velocity of flow of gas through the catalyst bed can preferably be from about 250 hr$^{-1}$ to about 25,000 hr$^{-1}$, more preferably, from about 500 hr$^{-1}$ to about 10,000 hr$^{-1}$.

The mixed alcohol synthesis process can produce a variety of hydrocarbons and oxygenated hydrocarbons as by-products. Regarding the mixed alcohol composition/product according to the invention, it can be desirable to operate the process so as to maximize not only the amount of methanol and ethanol formed, but also the amount of aldehydes and other oxygenates that can be particularly desirable in the OTO conversion process. It is particularly appropriate to maximize the amount of alcohols (e.g., particularly methanol and ethanol) formed in the mixed alcohol synthesis reaction, and to remove hydrocarbons less desirable in the conversion of oxygenates to olefins from the crude methanol product stream formed in the mixed alcohol synthesis reactor. In some embodiments, light hydrocarbon by-products (or unreacted reactants) can be reintroduced and/or recycled into the syngas formation process or into another step in the processes according to the invention.

6. Optionally Refining Crude Methanol to Make Methanol Product

In conventional methanol synthesis systems, the crude methanol product mixture formed in the alcohol synthesis unit is further processed after reaction to obtain a desirable methanol-containing composition. Processing can be accomplished by any known means. Examples of such means include, but are not limited to, distillation, selective condensation, and selective adsorption. Process conditions, e.g., temperatures and pressures, can vary according to the particular methanol composition desired. In some embodiments, it can be desirable to minimize the amount of water and light boiling point components in the methanol-containing composition, but without substantially reducing the amount of methanol, other desirable alcohols (e.g., ethanol), and/or other desirable oxygenates (e.g., aldehydes) that may also be present. In one embodiment, the crude methanol/ethanol stream is separated (e.g., distilled) to remove a portion of the undesirable components in the crude methanol stream; in a preferred embodiment, however, the crude mixed alcohol undergoes no distillation step.

Preferably, the mixed alcohol synthesis process is accomplished in the presence of a mixed alcohol synthesis catalyst and produces not only methanol but also a significant quantity of ethanol. As used herein, the terms "alcohol synthesis catalyst" and "mixed alcohol synthesis catalyst" should be understood to refer to compounds both that catalyze the conversion of syngas to alcohols (e.g., methanol and ethanol) and also that catalyze, facilitate, and/or support the water gas shift reaction.

It is preferred that the mixed alcohol product composition contains less than 97 wt % methanol, and contains an amount of ethanol effective in the catalytic conversion of the composition to olefin product. In one embodiment of the invention, the mixed alcohol product comprises at least about 40 wt % methanol, preferably, at least about 50 wt %, more preferably, at least about 60 wt % methanol, for example, at least about 70 wt % or at least about 75 wt %.

In another embodiment, the mixed alcohol product comprises not greater than about 96 wt % methanol, preferably, not greater than about 95 wt %, more preferably, not greater than about 94 wt %, for example, not greater than about 92 wt %.

In OTO processes, the yield of ethylene can be increased if there is a mix of ethanol and methanol in the oxygenate feed. Therefore, in yet another embodiment, the mixed alcohol composition/product recovered according to the process of the invention comprises greater than 10 ppm (w/w) ethanol, preferably, at least about 100 ppm (w/w), more preferably, at least about 1,000 ppm (w/w), still more preferably, at least about 10,000 ppm (w/w), most preferably, at least about 0.1 wt %.

In another embodiment, the recovered or final distilled mixed alcohol composition comprises not greater than 50 wt % ethanol, preferably, not greater than 40 wt %, more preferably, not greater than 35 wt %, most preferably, not greater than 30 wt % ethanol.

In another embodiment, the mixed alcohol product includes water. The water content should not be so high that shipping costs are prohibitive, but can advantageously be in sufficient quantity to affect the selectivity of the OTO process toward ethylene and/or propylene, e.g., to exert a positive partial pressure in the methanol-to-olefin conversion reaction, thereby increasing selectivity.

In one embodiment, the mixed alcohol composition/product contains at least about 0.1 wt % water, preferably, at least about 0.15 wt %, more preferably, at least about 0.2 wt %, most preferably, at least about 0.25 wt % water.

In a preferred embodiment, the mixed alcohol composition/product can contain not greater than about 20 wt % water, preferably, not greater than about 15 wt %, more preferably, not greater than about 10 wt %. In another embodiment, the mixed alcohol composition/product can contain not greater than about 2 wt % water, preferably, not greater than about 1.5 wt %, more preferably, not greater than about 1.2 wt %, most preferably, not greater than about 1 wt %.

In another embodiment, the mixed alcohol product can comprise at least about 0.7 wt % of one or more $C_3$-$C_4$ monoalcohols (e.g., n-propanol, isopropanol, n-butanol, isobutanol (2-methyl-1-propanol), 2-butanol, and the like), preferably, at least about 1 wt %, more preferably, at least about 2 wt %, for example, at least about 3 wt %.

In a preferred embodiment, the mixed alcohol product exhibits the following characteristics, and thus needs no further treatment for subsequent processes such as OTO reaction processes: (i) at least about 40 wt % methanol, (ii) at least about 3 wt % ethanol, (iii) at least about 0.7 wt % of one or more $C_3$-$C_4$ monoalcohols, (iv) not more than about 1 wt % $CO_2$, and (v) from about 0.05 wt % to about 20 wt % water. In another preferred embodiment, the mixed alcohol product exhibits the following characteristics, and thus needs no further treatment for subsequent processes such as OTO reaction processes: (i) at least about 50 wt % methanol, (ii) at least about 5 wt % ethanol, (iii) at least about 1 wt % of one or more $C_3$-$C_4$ monoalcohols, (iv) not more than about 0.8 wt % $CO_2$, and (v) from about 0.1 wt % to about 10 wt % water. In another embodiment, the mixed alcohol product exhibits the following characteristics, and thus needs no further treatment for subsequent processes such as OTO reaction processes: (i) at least about 60 wt % methanol, (ii) at least about 3 wt % ethanol, (iii) at least about 0.7 wt % of one or more $C_3$-$C_4$ monoalcohols, (iv) not more than about 1 wt % $CO_2$, and (v) from about 0.1 wt % to about 20 wt % water.

C. Integrated Production of Syngas and Mixed Alcohols

Another aspect of the invention relates to an integrated process for the production of mixed alcohols that combines a process of forming a syngas product from a hydrocarbon feedstock with a process of forming a mixed alcohol product from the formed syngas product. One non-limiting example of such an integrated process is shown in FIG. 1.

Figure 1:
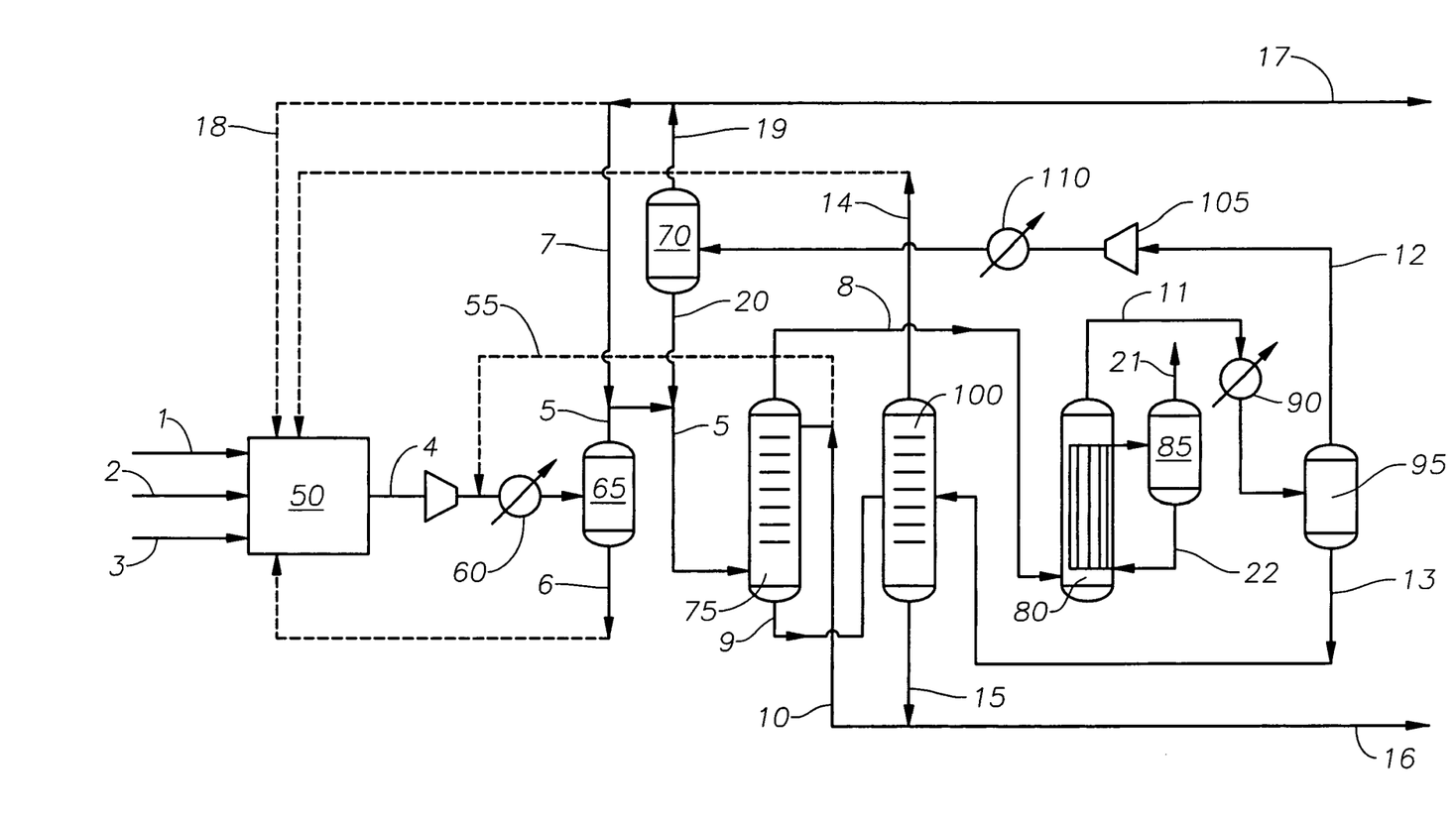
FIG. 1 is a schematic of one embodiment for forming olefins from natural gas according to the invention.

As shown in FIG. 1, a hydrocarbon feedstock containing natural gas (1), an oxygen source (2) such as oxygen and/or air, and a source of water (3) such as steam can be fed into a reformer (50) typically containing a reforming type catalyst, as mentioned above. To the hydrocarbon feedstock and/or to the reformer (50) can optionally be added condensed water (6), which may or may not contain mixed alcohols (from 55), carbon dioxide (14), and/or a first portion (18) of a recycled gas (19) containing an unreacted syngas composition (12). Of the remainder (7,17) of the recycled gas (19), typically a second portion (17) can be removed from the system as a purge gas.

After contacting the hydrocarbon feedstock with the catalyst in the reformer (50) under sufficient conditions, a syngas (4) is advantageously formed. In cases where the syngas (4) can contain undesirably high amounts of water, this syngas (4) is optionally but preferably, treated to remove at least a portion of the water before forming the syngas product (5) to be used as at least a portion of a feedstock for the mixed alcohol product formation process. Such treatment can include, but is not limited to, contacting the water-rich syngas (4) with a water-absorbent composition such as a mixed alcohol composition (55), chilling the water-rich syngas (4) in a chiller (60) to a temperature below about 0° C. and removing water (6) therefrom, and a combination thereof. The mixed alcohol composition (55) can be added from a separate source but is preferably, comprised of a portion of a mixed alcohol stream (i.e., from a mixed alcohol product (15) and/or a $CO_2$-lean mixed alcohol (10)). In a separator (65), a gas comprising the syngas product (5) can be separated from a liquid (6) comprising excess water, optionally mixed alcohol, and optionally other condensable components of the mixed alcohol composition (55).

The syngas product (5) can advantageously be combined with a third portion (7) of the recycled gas (19) containing unreacted syngas (12), as well as a recycle condensate (20) (which can be separated from the recycled gas (19) via the use of a separator/condenser (70) on the unreacted syngas composition (12)). This combined syngas product (5) can then advantageously be treated, e.g., in a $CO_2$ absorption column (75), to remove $CO_2$ therefrom by contacting the syngas product (5) with a $CO_2$-absorbent, preferably, low water content composition (e.g., a $CO_2$-lean mixed alcohol (10)) under process conditions sufficient to form a $CO_2$-lean syngas (8) and a $CO_2$-rich absorbent composition (e.g., a $CO_2$-rich mixed alcohol (9)).

The $CO_2$-lean syngas (8) can then be contacted with a mixed alcohol synthesis catalyst in an alcohol synthesis reactor (80) under conditions sufficient to form an initial mixed alcohol composition (11). While the alcohol synthesis reactor (80) is shown in FIG. 1 and described herein as a single vessel, it is contemplated that the initial mixed alcohol composition (11) can be formed in multiple vessels, in multiple stages within a single vessel, in multiple stages within multiple vessels, or some combination thereof, collectively designated as the alcohol synthesis reactor (80) herein. Optionally but preferably, excess heat of reaction can be removed from the alcohol synthesis reactor (80) by boiling water and producing steam (21). In a preferred embodiment, the steam can be produced in a thermosiphon boiler, where the steam/water mixture leaving the alcohol synthesis reactor (80) can be separated in a vessel (85). In this embodiment, the steam (21) can be removed from the system, or alternately recycled to the water source (3) input to the reformer (50) in the syngas formation process, while the water (22) can be returned to the alcohol synthesis reactor (80).

The initial mixed alcohol composition (11) can advantageously have its temperature reduced in a cooler (90) before being sent to a separator (95), in which is formed a liquid phase containing a crude mixed alcohol composition (13) and a gas phase containing unreacted syngas (12). The gas phase containing unreacted syngas (12) can advantageously be sent to a compressor (105) and a chiller (110) before being separated/condensed into recycle gas (19) and recycle condensate (20) in the previously mentioned separator (70).

The liquid phase containing the crude mixed alcohol composition (13), depending upon, inter alia, its $CO_2$ content and optionally also its water content, may either be sufficient for designation as a mixed alcohol product (e.g., at least a portion of which being used as a feedstock in a subsequent process such as an oxygenates-to-olefins process) or be sent to a stabilizer column (100) (i.e., essentially a $CO_2$ separator). At or before the stabilizer column (100), the $CO_2$-rich mixed alcohol (9), and optionally but preferably, also at least a portion of the crude mixed alcohol composition (13), can have $CO_2$ removed therefrom, thus forming a mixed alcohol product (15). The embodiment in FIG. 1 shows the mixed alcohol product (15) stream being split off into the $CO_2$-lean mixed alcohol (10) and another mixed alcohol product (16) stream; optionally, however, the $CO_2$-lean mixed alcohol (10) may be separately/externally supplied.

Advantageously, mixed alcohol products formed by the processes according to the invention can exhibit at least: (i) a methanol content of at least about 40 wt %, preferably, at least about 50 wt %, more preferably, at least about 60 wt %; (ii) an ethanol content of at least about 3 wt %, preferably, at least about 5 wt %, for example, at least about 7 wt % or at least about 10 wt %; and (iii) a $CO_2$ content of not more than about 1 mol %, preferably, not more than about 0.8 mol %, for example, not more than about 0.5 mol %.

Also advantageously, crude mixed alcohol compositions (e.g., 13), $CO_2$-lean mixed alcohols (e.g., 10), and mixed alcohol compositions (e.g., 55) formed by, and/or used in, the processes according to the invention can exhibit at least (i) a methanol content of at least about 40 wt %, preferably, at least about 50 wt %, more preferably, at least about 60 wt %; (ii) an ethanol content of at least about 3 wt %, preferably, at least about 5 wt %, for example, at least about 7 wt % or at least about 10 wt %; and (iii) optionally a $CO_2$ content of not more than about 3 mol %, preferably, not more than about 2 mol %, more preferably, not more than about 1 mol %, for example, not more than about 0.8 mol %.

In a preferred embodiment, compositions exhibiting a methanol content of at least about 40 wt %, an ethanol content of at least about 3 wt %, a $CO_2$ content of not more than about 1 mol %, and optionally a water content of not more than about 15 wt % (preferably, not more than about 10 wt %) may be used without further purification in a subsequent process, e.g., as at least a portion of an oxygenate feedstock in an OTO conversion system/process.

Also contemplated in this invention are processes for olefin formation, and potentially also processes for polyolefin formation (and/or copolymer formation in which olefins made according to the processes of the invention are used in the monomer feed), which can be integrated either with the integrated syngas formation-oxygenate formation process or with the oxygenate formation process alone.

D. Converting the Mixed Alcohol Product to Olefins

1. General Process Description

In one embodiment, the mixed alcohol product composition obtained according to this invention comprises at least a portion of an oxygenate feedstock that is converted to olefin(s) via contact with an olefin-forming catalyst to form the olefin product. The olefin product can then be recovered, and water, which generally forms during the conversion of the oxygenates in the mixed alcohol composition to olefins, can advantageously be removed. After removing the water, the olefins can be separated into individual olefin streams, with each individual olefin stream being available for further processing, if desired.

Although the present application is specifically directed to combining a methanol/ethanol synthesis system with an OTO reaction system, one or more additional components may be included in the feedstock that is directed to the OTO reaction system. For example, the feedstock that is directed to the OTO reaction system optionally contains, in addition to methanol and ethanol, one or more aliphatic-containing compounds such as alcohols, amines, carbonyl compounds for example, aldehydes, ketones and carboxylic acids, ethers, halides, mercaptans, sulfides, and the like, and mixtures thereof. The aliphatic moiety of the aliphatic-containing compounds typically contains from 1 to 50 carbon atoms, preferably, from 1 to 20 carbon atoms, more preferably, from 1 to 10 carbon atoms, most preferably, from 1 to 4 carbon atoms.

Non-limiting examples of aliphatic-containing compounds include: alcohols such as methanol, ethanol, n-propanol, isopropanol, and the like, alkyl-mercaptans such as methyl mercaptan and ethyl mercaptan, alkyl-sulfides such as methyl sulfide, alkyl amines such as methyl amine, alkyl ethers such as DME, diethyl ether and methyl ethyl ether, alkyl-halides such as methyl chloride and ethyl chloride, alkyl ketones such as dimethyl ketone, alkyl-aldehydes such as formaldehyde and acetaldehyde, and various organic acids such as formic acid and acetic acid.

The various feedstocks discussed above are converted primarily into one or more olefins. The olefins or olefin monomers produced from the feedstock typically have from 2 to 30 carbon atoms, preferably, 2 to 8 carbon atoms, more preferably, 2 to 6 carbon atoms, still more preferably, 2 to 4 carbons atoms, and most preferably, ethylene and/or propylene. Non-limiting examples of olefin monomer(s) include ethylene, propylene, butene-1, pentene-1,4-methyl-pentene-1, hexene-1, octene-1 and decene-1, preferably, ethylene, propylene, butene-1, pentene-1,4-methyl-pentene-1, hexene-1, octene-1 and isomers thereof. Other olefin monomers can include, but are not limited to, unsaturated monomers, diolefins having 4 to 18 carbon atoms, conjugated or nonconjugated dienes, polyenes, vinyl monomers, and cyclic olefins.

In a preferred embodiment, the feedstock, which contains methanol and ethanol, can be converted to olefin(s) in the presence of a molecular sieve catalyst composition into olefin(s) having 2 to 6 carbons atoms, preferably, 2 to 4 carbon atoms. The most preferred process is generally referred to as an oxygenate-to-olefins (OTO) reaction process. In an OTO process, typically an oxygenated feedstock, most preferably, a methanol- and ethanol-containing feedstock, is converted in the presence of a molecular sieve catalyst composition into one or more olefins, preferably, and predominantly, ethylene and/or propylene, referred to herein as light olefins.

In one embodiment, the amount of liquid feedstock, fed separately or jointly with a vapor feedstock, to a reactor system can be in the range from about 0.1 wt % to about 85 wt %, preferably, from about 1 wt % to about 75 wt %, more preferably, from about 5 wt % to about 65 wt %, based on the total weight of the feedstock (including any diluent contained therein). The liquid and vapor feedstocks can be of substantially the same composition, or contain varying proportions of the same or different feedstock components, optionally with the same or different diluent.

The conversion temperature employed in the conversion process, specifically within the reactor system, is typically from about 392° F. (200° C.) to about 1832° F. (1000° C.), preferably, from about 482° F. (250° C.) to about 1472° F. (800° C.), more preferably, from about 482° F. (250° C.) to about 1382° F. (750° C.), yet more preferably, from about 572° F. (300° C.) to about 1202° F. (650° C.), yet even more preferably, from about 662° F. (350° C.) to about 1112° F. (600° C.) most preferably, from about 662° F. (350° C.) to about 1022° F. (550° C.).

2. Description of Olefin-Forming Catalyst

Any catalyst capable of converting oxygenates to olefins can be used in this invention. Molecular sieve catalysts are preferred. Examples of such catalysts include zeolite-based, as well as non-zeolite-based, molecular sieves and can be of the large, medium, or small pore type. Molecular sieve materials all have 3-dimensional, four-connected framework structure of corner-sharing $TO_4$ tetrahedra, where T can be any tetrahedrally coordinated cation. These molecular sieves are typically described in terms of the size of the ring that defines a pore, where the size is based on the number of T atoms in the ring. Other framework-type characteristics include the arrangement of rings that form a cage, and, when present, the dimension of channels, and the spaces between the cages. See van Bekkum, et al., *Introduction to Zeolite Science and Practice, Second Completely Revised and Expanded Edition*, Volume 137, pp. 1-67, Elsevier Science, B. V., Amsterdam, Netherlands (2001).

Ideally, the molecular sieve catalyst composition comprises an alumina or a silica-alumina catalyst composition. Silicoaluminophosphate (SAPO) molecular sieve catalysts are particularly desirable in such conversion processes, because they are highly selective in the formation of ethylene and propylene. A non-limiting list of preferable SAPO molecular sieve catalyst compositions includes SAPO-17, SAPO-18, SAPO-34, SAPO-35, SAPO-44, the substituted forms thereof, and mixtures thereof. Preferably, the molecular sieve catalyst composition comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

Other non-limiting examples of molecular sieve catalyst compositions suitable for the processes of the invention can be found in, inter alia, U.S. Patent Application Publication No. 2005-0107482, which is fully incorporated by reference herein.

3. Adding Other Oxygenates to Mixed Alcohol Compositions

In an optional embodiment of this invention, the mixed alcohol composition can be converted into olefin(s) along with other oxygenates or diluents. The additional oxygenates or diluents can be co-mixed with the mixed alcohol composition, or can be added as a separate feed stream to an oxygenate conversion reactor in an OTO process. In one embodiment, the additional oxygenate includes one or more alcohols, preferably, aliphatic alcohol(s) where the aliphatic moiety of the alcohol(s) has from 3 to 10 carbon atoms, preferably, from 3 to 5 carbon atoms, and most preferably, from 3 to 4 carbon atoms. The alcohols include lower straight and branched chain aliphatic alcohols and their unsaturated counterparts. Non-limiting examples of additional oxygenates include n-propanol, isopropanol, methyl ethyl ether, dimethyl ether, diethyl ether, diisopropyl ether, methyl propyl ethers, ethyl propyl ethers, methyl butyl ethers such as methyl t-butyl ether, formaldehyde, dimethyl carbonate, dimethyl ketone, acetic acid, and mixtures thereof. In one embodiment, the feedstock for the OTO process can include, aside from methanol and ethanol, one or more of a propanol, dimethyl ether, diethyl ether, methyl t-butyl ether, acetic acid, or a combination thereof.

The mixed alcohol feedstock, in one embodiment, contains one or more diluent(s), typically used to reduce the concentration of alcohol (predominantly methanol), and are generally substantially non-reactive with the oxygenates in the feedstock and/or with the molecular sieve catalyst composition. Non-limiting examples of diluents include helium, argon, nitrogen, carbon monoxide, carbon dioxide, water, essentially non-reactive paraffins (e.g., alkanes such as methane, ethane, and propane), essentially non-reactive aromatic compounds, and mixtures thereof. In one embodiment, the amount of diluent in the feedstock can be from about 0.1 mol % to about 99 mol %, based on the total number of moles of the feedstock and any added diluent, preferably, from about 0.5 mol % to about 80 mol %, for example, from about 1 mol % to about 50 mol % or from about 3 mol % to about 25 mol %.

4. General Conditions for Converting Methanol/Ethanol to Olefins

According to the OTO reaction process of the invention, oxygenates can be contacted with an olefin-forming catalyst to form an olefin product, particularly a light olefin product such as ethylene and/or propylene. The process for converting a feedstock, especially a feedstock containing one or more oxygenates, in the presence of an olefin-forming molecular sieve catalyst composition of the invention, is carried out in a reaction process in a reactor, where the process is a fixed-bed process, a fluidized-bed process (includes a turbulent bed process), preferably, a continuous fluidized-bed process, and most preferably, a continuous high velocity fluidized-bed process.

The OTO reaction processes can take place in a variety of catalytic reactors, for instance, circulating fluidized-bed reactors, riser reactors, hybrid reactors that have a dense bed or fixed-bed reaction zones and/or fast fluidized-bed reaction zones coupled together, and the like. Suitable conventional reactor types can be found, for example, in U.S. Pat. Nos. 4,076,796 and 6,287,522, and in *Fluidization Engineering*, D. Kunii and O. Levenspiel, Robert E. Krieger Publishing Company, New York, N.Y. (1977), which is herein fully incorporated by reference.

One preferred reactor type is a riser reactor. These types of reactors are generally described, for example, in *Riser Reactor, Fluidization and Fluid-Particle Systems*, pp. 48 to 59, F. A. Zenz and D. F. Othmo, Reinhold Publishing Corporation, New York, 1960, in U.S. Pat. No. 6,166,282 (fast fluidized-bed reactor), and in U.S. patent application Ser. No. 09/564,613, filed May 4, 2000, (multiple riser reactor), which are all fully incorporated herein by reference.

In one embodiment, the average reaction temperature employed in the conversion process, specifically within the reactor, can be from about 250° C. to about 800° C., preferably, from about 250° C. to about 750° C., more preferably, from about 300° C. to about 650° C. or from about 350° C. to about 600° C., even more preferably, from about 350° C. to about 550° C. or from about 400° C. to about 500° C.

The pressure employed in the conversion process, specifically within the reactor, is generally not critical. The reaction pressure can desirably be based on the partial pressure of the feedstock, exclusive of any diluent therein. In one embodiment, the reaction pressure employed in the process ranges from about 0.1 kpaa (kPa abs.) to about 5 MPaa (MPa abs.), preferably, from about 5 kPaa to about 1 MPaa, most preferably, from about 20 kpaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock, excluding any diluents, to the reaction zone per hour per weight of molecular sieve in the molecular sieve catalyst composition in the reaction zone. The WHSV can advantageously be maintained at a level sufficient to keep the catalyst composition in a fluidized state within a reactor.

In one embodiment, the WHSV can range from about 1 $hr^{-1}$ to about 5000 $hr^{-1}$, preferably, from about 2 $hr^{-1}$ to about 3000 $hr^{-1}$, more preferably, from about 5 $hr^{-1}$ to about 1500 $hr^{-1}$, most preferably, from about 10 $hr^{-1}$ to about 1000 $hr^{-1}$. In a preferred embodiment, the WHSV can be greater than 20 $hr^{-1}$. Where a feedstock containing methanol and dimethyl ether is being converted, the WHSV can, in one embodiment, be from about 20 $hr^{-1}$ to about 300 $hr^{-1}$.

The superficial gas velocity (SGV) of the feedstock including diluent and reaction products within the reactor system can preferably, be sufficient to fluidize the molecular sieve catalyst composition within a reaction zone in the reactor system. In one embodiment, the SGV in the process, particularly within the reactor system, more particularly within the reaction zone of the riser reactor(s), can be at least 0.1 meter per second (m/sec), preferably, greater than about 0.5 m/sec, more preferably, greater than about 1 m/sec, even more preferably, greater than about 2 m/sec, yet even more preferably, greater than about 3 m/sec, and most preferably, greater than about 4 m/sec. See, for example, U.S. patent application Ser. No. 09/708,753, filed Nov. 8, 2000, the disclosure of which is fully incorporated herein by reference.

According to one embodiment, the conversion of oxygenate, particularly the conversion of methanol, to form olefin(s) is from about 90 wt % to about 98 wt %. According to another embodiment, the conversion of methanol-to-olefin(s) is from about 92 wt % to about 98 wt %, preferably, from about 94 wt % to about 98 wt %.

According to another embodiment, the conversion of methanol-to-olefin(s) can be above about 98 wt % to less than about 100 wt %. According to another embodiment, the conversion of methanol-to-olefin(s) can be from about 98.1 wt % to less than about 100 wt %; preferably, from about 98.2 wt % to about 99.8 wt %. According to another embodiment, the conversion of methanol-to-olefin(s) can be from about 98.2 wt % to less than about 99.5 wt %; preferably, from about 98.2 wt % to about 99 wt %.

It can be desirable to maintain an amount of coke on the catalyst in the reaction vessel, e.g., to enhance the formation of desired olefin product, particularly ethylene and propylene. For instance, in one embodiment, it is particularly desirable that the level of coke on the catalyst in the reactor be at least about 1.5 wt %, preferably, from about 2 wt % to about 30 wt %.

5. Impact of Ethylene-Propylene Ratio in OTO Reactions

It has been discovered that ethanol has a selectivity for ethylene under OTO and ETO reaction conditions, which approaches 100 weight percent. Methanol, in contrast, produces ethylene and propylene in generally equal amounts under OTO and ETO reaction conditions. By increasing the amount of ethanol contained in an OTO feedstock, the amount of ethylene produced in the OTO reaction system relative to propylene can be correspondingly increased. See, e.g., U.S. Patent Application Publication No. 2005-0107482, which is fully incorporated herein by reference, for further discussion of ethylene-propylene ratio and its impact on OTO reaction processes, inter alia.

E. Olefin Product Recovery and Use

In one embodiment, olefin product and other gases can be withdrawn from the reactor and passed through a recovery system. Any recovery system, technique, and/or sequence useful in separating olefin(s) and purifying olefin(s) from other gaseous components can be used in this invention. Examples of recovery systems can include, but are not limited to, one or more or a combination of various separation, fractionation, and/or distillation towers, columns, splitters, other associated equipment (e.g., various condensers, heat exchangers, refrigeration systems or chill trains, compressors, knock-out drums or pots, pumps, etc.), and the like, multiples, and combinations thereof.

Non-limiting examples of distillation towers, columns, splitters, or trains used alone or in combination can include one or more of a demethanizer (preferably, a high temperature demethanizer), a deethanizer, a depropanizer (preferably, a wet depropanizer), a wash tower often referred to as a caustic wash tower and/or quench tower, an absorber, an adsorber, a membrane, an ethylene ($C_2$) splitter, a propylene ($C_3$) splitter, a butene ($C_4$) splitter, and the like, multiples, and combinations thereof.

Various recovery systems useful for recovering predominately olefin(s), preferably, prime or light olefin(s) such as ethylene, propylene, and/or butane, are described, for example, in U.S. Pat. Nos. 5,960,643; 5,019,143; 5,452,581; 5,082,481; 5,672,197; 6,069,288; 5,904,880; 5,927,063; 6,121,504; 6,121,503; and 6,293,998, the disclosures of which are all fully incorporated herein by reference.

Generally, accompanying most recovery systems is the production, generation, and/or accumulation of additional products, by-products, and/or contaminants, along with the preferred products [e.g., prime olefin(s)]. The preferred prime products, i.e., light olefins such as ethylene and propylene, are typically purified for use in derivative manufacturing processes, such as polymerization processes. Therefore, in a preferred embodiment of the recovery system, the recovery system also includes a purification system. For example, the light olefin(s) produced, particularly in a MTO process, can be passed through a purification system that removes low levels of by-products and/or contaminants.

Non-limiting examples of contaminants and by-products include generally polar compounds, e.g., water, alcohols, carboxylic acids, ethers, carbon oxides, sulfur compounds (such as hydrogen sulfide, carbonyl sulfides, and mercaptans), ammonia and other nitrogenated compounds, arsine, phosphine, chlorides, and the like, and combinations thereof. Other contaminants and by-products can include, but are not limited to, hydrogen and hydrocarbons such as acetylene, methyl acetylene, propadiene, butadiene, butyne, and the like, and combinations thereof.

Other recovery systems including purification systems, for example, for the purification of olefin(s), are described in *Kirk-Othmer Encyclopedia of Chemical Technology*, 4th Edition, Vol. 9, John Wiley & Sons, 1996, pp. 249-271 and 894-899, which is fully incorporated herein by reference. Purification systems are also described in, for example, U.S. Pat. Nos. 6,271,428; 6,293,999; and U.S. patent application Ser. No. 09/689,363, filed Oct. 20, 2000, the disclosures of which are fully incorporated herein by reference.

F. Oligomerization/Polymerization of Olefin Product

The ethylene and propylene streams produced and recovered according to this invention can be polymerized to form oligomeric, polymeric, and/or plastic compositions, e.g., polyolefins, particularly oligomers, homopolymers, copolymers, and/or blends of monomers, such as ethylene and propylene, formed by a process according to this invention. Any suitable process for forming polyethylene and/or polypropylene oligomers, homopolymers, copolymers, and/or blends can be used. Catalytic polymerization processes are typically preferred. Particularly preferred are metallocene, Ziegler/Natta, aluminum oxide, and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment, the ethylene or propylene product can be contacted with a metallocene catalyst to form an oligoolefin or a polyolefin (hereinafter, collectively "polyolefin"). In some embodiments, the polyolefin-forming process can be carried out at a temperature from about 50° C. to about 320° C., and/or at low, medium, or high pressure, being anywhere from below about 1 barg (1.02 kg/cm² gauge) to about 3200 barg (3264 kg/cm² gauge). For processes desired to be carried out in solution, an inert diluent can be used. In this type of operation, it can be desirable that the pressure range from about 10 barg (10.2 kg/cm² gauge) to about 150 barg (1.53 kg/cm² gauge), and preferably, at a temperature from about 120° C. to about 250° C. For gas phase processes, it can be desirable that the temperature generally be from about 60° C. to about 120° C., and that the operating pressure range from about 5 barg (5.1 kg/cm² gauge) to about 50 barg (51 kg/cm² gauge).

In addition to polyolefins, numerous other olefin derivatives may be formed from the olefin products (e.g., ethylene, propylene, and $C_{4+}$ olefins, particularly butylenes) manufactured according to the invention. The olefins manufactured according to the invention can also be used to synthesize such compounds as aldehydes, acids such as $C_2$-$C_{13}$ mono carboxylic acids, alcohols such as $C_2$-$C_{12}$ mono alcohols, esters that can be made from the $C_2$-$C_{12}$ mono carboxylic acids and the $C_2$-$C_{12}$ mono alcohols, linear alpha-olefins, vinyl acetate, ethylene dichloride and vinyl chloride, ethylbenzene, ethylene oxide, cumene, acrolein, allyl chloride, propylene oxide, acrylic acid, ethylene-propylene rubbers, acrylonitrile, trimers and dimers of ethylene and propylene, and the like, and blends and copolymers and combinations thereof. The $C_{4+}$ olefins, butylene in particular, are particularly suited for the manufacture of aldehydes, acids, alcohols, esters that can be made from $C_5$-$C_{13}$ mono carboxylic acids and $C_5$-$C_{13}$ mono alcohols, and linear alpha-olefins.

G. Examples

The present invention can be better understood in view of the following non-limiting example, which represents a process simulation using Pro/II™ software commercially available from Simulation Sciences. Thermodynamic equilibrium at reactor outlet conditions was a boundary condition for all compositions in each of the syngas generation, methanol synthesis, and water-gas shift reactions. In addition, the reactions for conversion of syngas to ethanol and higher ($C_{2+}$) alcohols were selected to achieve a desirable mixed alcohol composition. Further, the $CO_2$ absorption process was simulated using a vapor-liquid equilibrium (VLE) thermodynamic package.

Example I

Mixed Alcohol Product Synthesis Process According to the Invention

Example I describes the synthesis of a mixed alcohol product according to the following conditions:

| Reformer conditions | Feedstock | Natural gas, air, steam |
|---|---|---|
| | Pressure | 48 bar (~49 kg/cm² abs.) |
| | Oxygen:Carbon ratio | 0.42 |
| | Steam:Carbon ratio | 1.5 |
| | Final equilibrium temp. | 1025° C. |
| Mixed alcohol product | Methanol | 72.2 wt % |
| | Ethanol | 19.4 wt % |
| | Propanol | 3.1 wt % |
| | Water | 5.0 wt % |
| | Carbon dioxide | 0.3 wt % |
| Alcohol synthesis conditions | Pressure | 90 bar (~92 kg/cm² abs.) |
| | Exit equilibrium temp. (temp. where alcohol synthesis equilibrium calculated) | 270° C. |
| | $CH_4$ selectivity (per pass) | 2.1% |
| $CO_2$ absorption conditions | Pressure | 90 bar (~92 kg/cm² abs.) |
| | Temperature | -30° C. |
| | $CO_2$ absorption (per pass) | 91.4% |

Information collected at each step of the integrated process, which was conducted using the integrated syngas-oxygenate formation process and apparatuses described in FIG. 1 and section C herein, is shown in Tables 1 and 2.

TABLE 1

| | Stream Number | | | | | | | | | |
|---|---|---|---|---|---|---|---|---|---|---|
| | 1 | 2 | 3 | 4 | 5 | 6 | 7 | 8 | 9 | 10 |
| Stream Description | natural gas | oxygen to reformer | steam to reformer | syngas from reformer | HP syngas | water-alcohol recycle | recycle syngas | syngas feed to synthesis reactor | rich alcohol | lean alcohol |
| Phase | Vapor | Vapor | Vapor | Vapor | Vapor | Mixed | Vapor | Vapor | Liquid | Liquid |
| Temp [° C.] | 48.0 | 300.0 | 300.0 | 48.0 | -30.0 | 17.4 | -30.0 | -30.0 | -30.0 | -29.0 |
| Pressure [Bar] | 45 | 45 | 48 | 20 | 90 | 90 | 90 | 90 | 90 | 90 |
| Flow rate [$10^3$ kg-mol/hr] | 30 | 12 | 44 | 119 | 119 | 1 | 160 | 264 | 114 | 100 |
| Total Mass Rate [$10^3$ kg/hr] | 500 | 387 | 793 | 1629 | 1615 | 14 | 1509 | 2584 | 3862 | 3323 |
| Total Mol. Wt. | 16.71 | 32.00 | 18.02 | 13.63 | 13.60 | 18.70 | 9.43 | 9.77 | 33.78 | 33.23 |
| | | | | Molar Composition | | | | | | |
| WATER | 0.0% | 0.0% | 100.0% | 0.6% | 0.0% | 97.0% | 0.0% | 0.0% | 8.0% | 9.2% |
| NITROGEN | 5.5% | 0.0% | 0.0% | 4.8% | 4.8% | 0.0% | 21.9% | 15.1% | 0.7% | 0.0% |
| CMONOXIDE | 0.0% | 0.0% | 0.0% | 27.2% | 27.3% | 0.2% | 2.1% | 13.2% | 0.9% | 0.0% |
| OXYGEN | 0.0% | 100.0% | 0.0% | 0.0% | 0.0% | 0.0% | 0.0% | 0.0% | 0.0% | 0.0% |
| CDIOXIDE | 0.0% | 0.0% | 0.0% | 7.5% | 7.6% | 2.7% | 1.9% | 0.4% | 9.8% | 0.2% |
| METHANE | 94.5% | 0.0% | 0.0% | 0.3% | 0.3% | 0.0% | 2.6% | 1.6% | 0.3% | 0.0% |
| METHANOL | 0.0% | 0.0% | 0.0% | 0.0% | 0.0% | 0.0% | 0.1% | 0.0% | 65.4% | 74.9% |
| ETHANOL | 0.0% | 0.0% | 0.0% | 0.0% | 0.0% | 0.0% | 0.0% | 0.0% | 12.2% | 14.0% |
| ISOPROPANOL | 0.0% | 0.0% | 0.0% | 0.0% | 0.0% | 0.0% | 0.0% | 0.0% | 1.5% | 1.7% |
| HYDROGEN | 0.0% | 0.0% | 0.0% | 59.6% | 60.0% | 0.2% | 71.5% | 69.7% | 1.2% | 0.0% |
| | | | | Weight Composition | | | | | | |
| WATER | 0.0% | 0.0% | 100.0% | 0.8% | 0.0% | 93.4% | 0.0% | 0.0% | 4.3% | 5.0% |
| NITROGEN | 9.3% | 0.0% | 0.0% | 9.9% | 9.9% | 0.0% | 64.9% | 43.3% | 0.5% | 0.0% |
| CMONOXIDE | 0.0% | 0.0% | 0.0% | 55.9% | 56.3% | 0.2% | 6.2% | 37.7% | 0.7% | 0.0% |
| OXYGEN | 0.0% | 100.0% | 0.0% | 0.0% | 0.0% | 0.0% | 0.0% | 0.0% | 0.0% | 0.0% |
| CDIOXIDE | 0.0% | 0.0% | 0.0% | 24.3% | 24.5% | 6.3% | 9.0% | 1.8% | 12.8% | 0.3% |
| METHANE | 90.7% | 0.0% | 0.0% | 0.4% | 0.4% | 0.0% | 4.5% | 2.7% | 0.1% | 0.0% |
| METHANOL | 0.0% | 0.0% | 0.0% | 0.0% | 0.0% | 0.0% | 0.2% | 0.2% | 62.1% | 72.2% |
| ETHANOL | 0.0% | 0.0% | 0.0% | 0.0% | 0.0% | 0.0% | 0.0% | 0.0% | 16.7% | 19.4% |
| ISOPROPANOL | 0.0% | 0.0% | 0.0% | 0.0% | 0.0% | 0.0% | 0.0% | 0.0% | 2.7% | 3.1% |
| HYDROGEN | 0.0% | 0.0% | 0.0% | 8.8% | 8.9% | 0.0% | 15.3% | 14.4% | 0.1% | 0.0% |

TABLE 2

| | Stream Number | | | | | | | | | |
|---|---|---|---|---|---|---|---|---|---|---|
| | 11 | 12 | 13 | 14 | 15 | 16 | 17 | 18 | 19 | 20 |
| Stream Description | synthesis reactor effluent | unreacted syngas | crude alcohol product | stabilizer overhead | stabilizer bottoms | mixed alcohol product | purge gas | recycle purge to reformer | recycle syngas | condensate from recycle syngas |
| Phase | Vapor | Vapor | Liquid | Vapor | Liquid | Liquid | Vapor | Vapor | Vapor | Liquid |
| Temp [° C.] | 270.0 | 48.0 | 48.0 | −30.1 | 167.7 | 48.0 | −30.0 | −30.0 | −30.0 | −30.0 |
| Pressure [Bar] | 90 | 90 | 90 | 20 | 20 | 20 | 90 | 90 | 90 | 90 |
| Flow rate [$10^3$ kg-mol/hr] | 208 | 183 | 25 | 15 | 126 | 26 | 7 | 14 | 181 | 1 |
| Total Mass Rate [$10^3$ kg/hr] | 2582 | 1756 | 826 | 562 | 4172 | 849 | 67 | 135 | 1711 | 45 |
| Total Mol. Wt. | 12.41 | 9.61 | 32.70 | 36.42 | 33.23 | 33.23 | 9.43 | 9.43 | 9.43 | 33.72 |
| Molar Composition | | | | | | | | | | |
| WATER | 1.1% | 0.0% | 9.0% | 0.0% | 9.2% | 9.2% | 0.0% | 0.0% | 0.0% | 3.0% |
| NITROGEN | 19.2% | 21.7% | 0.9% | 6.3% | 0.0% | 0.0% | 21.9% | 21.9% | 21.9% | 0.8% |
| CMONOXIDE | 1.8% | 2.1% | 0.1% | 6.6% | 0.0% | 0.0% | 2.1% | 2.1% | 2.1% | 0.1% |
| OXYGEN | 0.0% | 0.0% | 0.0% | 0.0% | 0.0% | 0.0% | 0.0% | 0.0% | 0.0% | 0.0% |
| CDIOXIDE | 1.8% | 2.0% | 0.8% | 73.1% | 0.2% | 0.2% | 1.9% | 1.9% | 1.9% | 9.0% |
| METHANE | 2.3% | 2.6% | 0.2% | 2.6% | 0.0% | 0.0% | 2.6% | 2.6% | 2.6% | 0.4% |
| METHANOL | 9.3% | 0.6% | 71.8% | 0.0% | 74.9% | 74.9% | 0.1% | 0.1% | 0.1% | 76.4% |
| ETHANOL | 1.7% | 0.1% | 13.8% | 0.0% | 14.0% | 14.0% | 0.0% | 0.0% | 0.0% | 8.4% |
| ISOPROPANOL | 0.2% | 0.0% | 1.7% | 0.0% | 1.7% | 1.7% | 0.0% | 0.0% | 0.0% | 0.9% |
| HYDROGEN | 62.5% | 70.9% | 1.7% | 11.4% | 0.0% | 0.0% | 71.5% | 71.5% | 71.5% | 1.0% |
| Weight Composition | | | | | | | | | | |
| WATER | 1.6% | 0.0% | 5.0% | 0.0% | 5.0% | 5.0% | 0.0% | 0.0% | 0.0% | 1.6% |
| NITROGEN | 43.3% | 63.3% | 0.7% | 4.9% | 0.0% | 0.0% | 64.9% | 64.9% | 64.9% | 0.6% |
| CMONOXIDE | 4.1% | 6.0% | 0.1% | 5.1% | 0.0% | 0.0% | 6.2% | 6.2% | 6.2% | 0.1% |
| OXYGEN | 0.0% | 0.0% | 0.0% | 0.0% | 0.0% | 0.0% | 0.0% | 0.0% | 0.0% | 0.0% |
| CDIOXIDE | 6.5% | 9.0% | 1.0% | 88.3% | 0.3% | 0.3% | 9.0% | 9.0% | 9.0% | 11.7% |
| METHANE | 3.0% | 4.4% | 0.1% | 1.1% | 0.0% | 0.0% | 4.5% | 4.5% | 4.5% | 0.2% |
| METHANOL | 23.9% | 2.0% | 70.4% | 0.0% | 72.2% | 72.2% | 0.2% | 0.2% | 0.2% | 72.6% |
| ETHANOL | 6.4% | 0.3% | 19.4% | 0.0% | 19.4% | 19.4% | 0.0% | 0.0% | 0.0% | 11.5% |
| ISOPROPANOL | 1.0% | 0.0% | 3.1% | 0.0% | 3.1% | 3.1% | 0.0% | 0.0% | 0.0% | 1.6% |
| HYDROGEN | 10.2% | 14.9% | 0.1% | 0.6% | 0.0% | 0.0% | 15.3% | 15.3% | 15.3% | 0.1% |

Because of the requirements of most OTO processes, not only the mixed alcohol product (15,16) but also the crude mixed alcohol composition (13) are suitable for use in a subsequent OTO process according to the invention, notably even without a treatment step, e.g., to remove excess water. Indeed, a distinct advantage of the integrated process of Example I is the capability to produce the mixed alcohol product using a minimum (or at least a relatively small number) of processing steps to achieve (i) a sufficiently low $CO_2$-content syngas, thus improving the yield of ethanol in the alcohol processing step, and (ii) a mixed alcohol product with sufficiently low $CO_2$ content and acceptably low water content, such that no further processing steps are needed before use in an oxygenates-to-olefins process.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for producing a mixed alcohol product, said process comprising:
   a. contacting a feed stream comprising a syngas with a $CO_2$-lean mixed alcohol under process conditions sufficient to form a $CO_2$-lean syngas and a $CO_2$-rich mixed alcohol;
   b. contacting the $CO_2$-lean syngas with an alcohol synthesis catalyst under conditions sufficient to form a liquid comprising a crude mixed alcohol composition and a gas comprising unreacted syngas wherein the $CO_2$-rich mixed alcohol and the crude mixed alcohol composition are combined before $CO_2$ removal; and
   c. removing $CO_2$ from the $CO_2$-rich mixed alcohol and the crude mixed alcohol composition, to form the mixed alcohol product, which comprises at least about 40 wt % methanol, at least about 3 wt % ethanol, from about 0.25 wt % to about 10 wt % water and no more than about 1 mol % $CO_2$.

2. The process of claim 1, wherein a portion of the mixed alcohol product forms at least a portion of the $CO_2$-lean mixed alcohol.

3. The process of claim 1, wherein the feed stream further comprises at least a portion of the gas.

4. The process of claim 1, wherein the $CO_2$ removal from the $CO_2$-rich mixed alcohol and the crude mixed alcohol composition is accomplished by depressurization, distillation, or both.

5. The process of claim 1, further comprising:
   d. removing water from the feed stream before contacting with the $CO_2$-lean mixed alcohol for absorbing $CO_2$.

6. The process of claim 5, further comprising:
   e. contacting natural gas, an oxygen source, and a water source under conditions sufficient to form the syngas; and f. recycling at least a portion of the $CO_2$, separated from the combined $CO_2$-rich mixed alcohol and crude mixed alcohol composition, for combining with the natural gas, oxygen source, and water source to form the syngas.

7. The process of claim 5, wherein the water is removed by:
   (i) chilling the syngas to a temperature below about 0° C. and isolating condensed water therefrom;
   (ii) contacting the syngas with a $CO_2$-lean alcohol composition; or (iii) both (i) and (ii).

8. The process of claim 7, wherein the syngas is contacted with the $CO_2$-lean alcohol composition, and wherein a portion of the mixed alcohol product forms at least a portion of the $CO_2$-lean alcohol composition.

9. The process of claim 7, wherein the condensed water is isolated from the chilled syngas, and wherein the condensed water and, optionally, at least a portion of the $CO_2$-lean alcohol composition are recycled to step d.

10. The process of claim 1, wherein the crude mixed alcohol composition and the $CO_2$-lean mixed alcohol each comprise at least about 40 wt % methanol and at least about 3 wt % ethanol.

11. The process of claim 10, wherein the crude mixed alcohol composition comprises one or more of the following:
    (i) at least about 50 wt % methanol;
    (ii) at least about 5 wt % ethanol;
    (iii) at least about 1 wt % of one or more $C_3$-$C_4$ monoalcohols;
    (iv) not more than about 3 wt % $CO_2$; and
    (v) from about 0.25 wt % to about 10 wt % water.

12. The process of claim 10, wherein the mixed alcohol product, prior to any treatment step, comprises one or more of the following:
    (i) at least about 50 wt % methanol;
    (ii) at least about 5 wt % ethanol;
    (iii) at least about 1 wt % of one or more $C_3$-$C_4$ monoalcohols;
    (iv) not more than about 0.8 wt % $CO_2$; and
    (v) from about 0.1 wt % to about 10 wt % water.

13. The process of claim 1, wherein the alcohol synthesis catalyst comprises a copper-containing catalyst.

14. The process of claim 13, wherein the copper-containing catalyst comprises a copper oxide.

15. The process of claim 1, wherein the contacting of the $CO_2$-lean syngas with the alcohol synthesis catalyst occurs at a temperature from more than 250° C. to about 320° C. and at a pressure from about 30 barg (30.6 kg/cm² gauge) to about 150 barg (153 kg/cm² gauge).

16. The process of claim 1, wherein the contacting of the $CO_2$-lean syngas with the alcohol synthesis catalyst occurs within a single reaction vessel.

17. A process for producing a mixed alcohol product, said process comprising:
    a. contacting a feed stream comprising a syngas with a $CO_2$-lean mixed alcohol under process conditions sufficient to form a $CO_2$-lean syngas and a $CO_2$-rich mixed alcohol;
    b. contacting the $CO_2$-lean syngas with an alcohol synthesis catalyst at a temperature from more than 250° C. to about 320° C. and at a pressure from about 30 barg (30.6 kg/cm² gauge) to about 150 barg (153 kg/cm² gauge) to form a liquid comprising a crude mixed alcohol composition and a gas comprising unreacted syngas, wherein the $CO_2$-rich mixed alcohol and the crude mixed alcohol composition are combined before $CO_2$ removal; and
    c. removing $CO_2$ from the $CO_2$-rich mixed alcohol and the crude mixed alcohol composition, to form the mixed alcohol product, which comprises no more than about 1 mol% $CO_2$,
    wherein the $CO_2$-lean mixed alcohol and the mixed alcohol product each comprise at least about 40 wt % methanol, from about 0.25 wt % to about 10 wt % water and at least about 3 wt % ethanol.

18. A process for producing a mixed alcohol product, said process comprising:
    a. contacting a feed stream comprising a syngas with a $CO_2$-lean mixed alcohol under process conditions sufficient to form a $CO_2$-lean syngas and a $CO_2$-rich mixed alcohol;
    b. contacting the $CO_2$-lean syngas with an alcohol synthesis catalyst under conditions sufficient to form a liquid comprising a crude mixed alcohol composition and a gas comprising unreacted syngas, wherein the $CO_2$-rich mixed alcohol and the crude mixed alcohol composition are combined before $CO_2$ removal; and
    c. removing $CO_2$ from the $CO_2$-rich mixed alcohol and the crude mixed alcohol composition, to form the mixed alcohol product, which comprises at least about 40 wt % methanol, at least about 3 wt % ethanol, from about 0.25 wt % to about 10 wt % water and no more than about 1 mol % $CO_2$, wherein a portion of the mixed alcohol product forms at least a portion of the $CO_2$-lean mixed alcohol.

19. The process of claim 18, wherein the $CO_2$-lean syngas is contacted with the alcohol synthesis catalyst at a temperature from more than 250° C. to about 320° C. and at a pressure from about 30 barg (30.6 kg/cm² gauge) to about 150 barg (153 kg/cm² gauge).

\* \* \* \* \*